(12) United States Patent
Hagihara et al.

(10) Patent No.: US 12,187,764 B2
(45) Date of Patent: Jan. 7, 2025

(54) AFFINITY CARRIER USING MUTANT VHH ANTIBODY

(71) Applicant: JSR CORPORATION, Minato-ku (JP)

(72) Inventors: Yoshihisa Hagihara, Tsukuba (JP); Yoko Akazawa, Ikeda (JP); Yuji Ito, Kagoshima (JP); Tomonari Matsuda, Otsu (JP); Norihiko Kiyose, Kumamoto (JP); Nobuo Miyazaki, Kumamoto (JP); Tetsuo Fukuta, Minato-ku (JP); Yusaku Mizuguchi, Minato-ku (JP)

(73) Assignee: JSR CORPORATION, Minato-ku (JP)

( * ) Notice: Subject to any disclaimer, the term of this patent is extended or adjusted under 35 U.S.C. 154(b) by 926 days.

(21) Appl. No.: 17/253,372

(22) PCT Filed: Jun. 20, 2019

(86) PCT No.: PCT/JP2019/024404
§ 371 (c)(1),
(2) Date: Dec. 17, 2020

(87) PCT Pub. No.: WO2019/244961
PCT Pub. Date: Dec. 26, 2019

(65) Prior Publication Data
US 2021/0261606 A1    Aug. 26, 2021

(30) Foreign Application Priority Data
Jun. 20, 2018   (JP) ................................. 2018-117403

(51) Int. Cl.
| C07K 16/00 | (2006.01) |
| C07K 1/22 | (2006.01) |
| C07K 16/42 | (2006.01) |
| C07K 17/00 | (2006.01) |

(52) U.S. Cl.
CPC ............... *C07K 1/22* (2013.01); *C07K 16/00* (2013.01); *C07K 16/4258* (2013.01); *C07K 17/00* (2013.01); *C07K 2317/569* (2013.01)

(58) Field of Classification Search
None
See application file for complete search history.

(56) References Cited

U.S. PATENT DOCUMENTS

| 2018/0094056 A1 | 4/2018 | Mathieu et al. |
| 2019/0016752 A1 | 1/2019 | Lu et al. |

FOREIGN PATENT DOCUMENTS

| WO | WO 2010/130677 A1 | 11/2010 |
| WO | WO 2016/205531 A2 | 12/2016 |
| WO | WO 2017/114495 A1 | 7/2017 |

OTHER PUBLICATIONS

Davenport et al., Journal of Chromatography B, 1021 (2016) 114-121.*
Kumada et al., Biochimica et Biophysica Acta 1844 (2014) 1960-1969.*
Edwards et al., J. Mol. Biol. (2003) 334, 103-118.*
Ikeuchi et al., Nature Portfolio, 11:20624, https://doi.org/10.1038/s41598-021-98977-8, Oct. 2021, downloaded Sep. 28, 2023.*
International Search Report issued Sep. 17, 2019 in PCT/JP2019/024404 filed Jun. 20, 2019, 2 pages.
"One-step immunoprecipitation method of MBP using Nanobocy (VHH) MBP-Trap, column of Features of MBP-Trap_A"), Nanobody (VHH) MBP, MBP-Trap, 2019 [retrieved on Aug. 30, 2019], 4 total pages.
Extended European Search Report issued Feb. 9, 2022 in European Patent Application No. 19822914.8, 8 pages.
Carola W.N. Damen, et al., "The bioanalysis of the monoclonal antibody trastuzumab by high-performance liquid chromatography with fluorescence detection after immuno-affinity purification from human serum," Journal of Pharmaceutical and Biomedical Analysis, vol. 50, No. 5, 2009, pp. 861-866.
Jinheng Fu, et al., "One-step orientated immobilization of nanobodies and its application for immunoglobulin purification," Journal of Chromatography A, vol. 1603, 2019, pp. 15-22.

* cited by examiner

*Primary Examiner* — Marianne P Allen
(74) *Attorney, Agent, or Firm* — Oblon, McClelland, Maier & Neustadt, L.L.P.

(57) ABSTRACT

Provision of an affinity carrier using a mutant VHH antibody. An affinity carrier comprising: a solid phase carrier; and an immunoglobulin-binding protein bound to the solid phase carrier; wherein the immunoglobulin-binding protein comprises a mutant VHH antibody or a fragment of the mutant VHH antibody that recognizes an epitope in at least one region selected from the group consisting of amino acids 127 to 184 of SEQ ID NO: 22 and amino acids 13 to 210 of SEQ ID NO: 23.

4 Claims, 2 Drawing Sheets

Specification includes a Sequence Listing.

AFFINITY CARRIER USING MUTANT VHH ANTIBODY

FIELD OF THE INVENTION

The present invention relates to an affinity carrier using a mutant VHH antibody and a method for isolating a target substance with the affinity carrier.

BACKGROUND OF THE INVENTION

Protein preparations, representatively antibody drugs, are basically composed of monoclonal antibodies which are produced in large scale by cell culture techniques. Affinity chromatography is typically used in an early stage of purification for the production of antibody drugs. Currently, commercially available antibody drugs are mainly composed of antibodies belonging to immunoglobulin G (IgG) subclasses. In an early stage of purification of IgG subclass antibodies, affinity chromatography utilizing Protein A, one of the cell wall proteins produced by a gram-positive bacterium *Staphylococcus aureus*, is generally used as a ligand. While, recently, development of modified antibodies such as partial antibodies, antibody-drug conjugates, and bispecific antibodies have been especially carried out for improving the functionality of antibody drugs. For affinity purification of these modified antibodies, development of affinity carrier using a ligand having a property different from that of Protein A has been carried out and put on the market.

VHH (variable domain of heavy chain of heavy-chain antibody) is a domain comprising a variable domain of a heavy-chain antibody with no light-chain contained in sera of Artiodactyla camelids (such as *Camelus bactrianus*, *Camelus dromedarius*, and *Lama glama*). VHH is a minimum component of an immunoglobulin fragment which can bind to an antigen and therefore is useful as a component of antibody drugs and a ligand of affinity carriers.

SUMMARY OF THE INVENTION

Problem to be Solved by the Invention

The present invention provides an affinity carrier to which a mutant VHH antibody useful as an antibody-binding ligand is immobilized.

Means for Solving the Problem

The present invention provides the followings.
[1] An affinity carrier comprising:
a solid phase carrier; and
an immunoglobulin-binding protein bound to the solid phase carrier,
wherein the immunoglobulin-binding protein comprises a mutant VHH antibody or a fragment of the mutant VHH antibody that recognizes an epitope in at least one region selected from the group consisting of amino acids 127 to 184 of SEQ ID NO: 22 and amino acids 13 to 210 of SEQ ID NO: 23.
[2] The affinity carrier according to [1], wherein the mutant VHH antibody comprises a complementarity-determining region having at least one histidine inserted into a pre-mutation VHH antibody or at least one amino acid residue substituted with histidine.
[3] The affinity carrier according to [2], wherein the pre-mutation VHH antibody is a polypeptide consisting of an amino acid sequence having an identity of at least 85% to any of amino acid sequences of SEQ ID NOS: 1, 2, 3 and 4 and having an affinity for a Fab region of trastuzumab.
[4] The affinity carrier according to [2] or [3], wherein the complementarity-determining region is CDR3.
[5] The affinity carrier according to [4], wherein the mutant VHH antibody is a polypeptide consisting of an amino acid sequence having an identity of at least 85% to the amino acid sequence of SEQ ID NO: 1 in which at least at one amino acid residue at position selected from the group consisting of positions corresponding to amino acids 97, 100, and 102 of SEQ ID NO: 1 is substituted with histidine.
[6] The affinity carrier according to any one of [3] to [5], wherein an amino acid sequence having an identity of at least 85% to the amino acid sequence of SEQ ID NO: 1 has amino acid sequences of SEQ ID NO: 10, SEQ ID NO: 11, and SEQ ID NO: 12 at CDR1, CDR2, and CDR3 corresponding to amino acids 26 to 35, 51 to 65, and 96 to 107 of SEQ ID NO: 1, respectively,
an amino acid sequence having an identity of at least 85% to the amino acid sequence of SEQ ID NO: 2 has amino acid sequences of SEQ ID NO: 13, SEQ ID NO: 14, and SEQ ID NO: 15 at CDR1, CDR2, and CDR3 corresponding to amino acids 26 to 37, 53 to 68, and 99 to 118 of SEQ ID NO: 2, respectively,
an amino acid sequence having an identity of at least 85% to the amino acid sequence of SEQ ID NO: 3 has amino acid sequences of SEQ ID NO: 16, SEQ ID NO: 17, and SEQ ID NO: 18 at CDR1, CDR2, and CDR3 corresponding to amino acids 26 to 35, 51 to 66, and 97 to 116 of SEQ ID NO: 3, respectively, and
an amino acid sequence having an identity of at least 858 to the amino acid sequence of SEQ ID NO: 4 has amino acid sequences of SEQ ID NO: 19, SEQ ID NO: 20, and SEQ ID NO: 21 at CDR1, CDR2, and CDR3 corresponding to amino acids 26 to 35, 51 to 66, and 97 to 116 of SEQ ID NO: 4, respectively.
[7] The affinity carrier according to any one of [2] to [6], wherein the mutant VHH antibody consists of an amino acid sequence in which at least one lysine in the amino acid sequence of the pre-mutation VHH antibody is substituted with arginine.
[8] The affinity carrier according to [1], wherein the mutant VHH antibody consists of an amino acid sequence in which at least one lysine in an amino acid sequence of a pre-mutation VHH antibody is substituted with arginine.
[9] The affinity carrier according to [8], wherein the pre-mutation VHH antibody is a polypeptide consisting of an amino acid sequence having an identity of at least 85% to an amino acid sequence of SEQ ID NO: 1 and having an affinity for a Fab domain of trastuzumab.
[10] The affinity carrier according to [9], wherein the mutant VHH antibody is a polypeptide consisting of an amino acid sequence having an identity of at least 85% to the amino acid sequence of SEQ ID NO: 1 in which at least at one position selected from the group consisting of positions corresponding to amino acids 43, 53, 64, 75, and 86 of SEQ ID NO: 1 is arginine.
[11] The affinity carrier according to [9] and [10], wherein the amino acid sequence having an identity of at least 85% to the amino acid sequence of SEQ ID NO: 1 has amino acid sequences of SEQ ID NO: 10, SEQ ID NO: 11, and SEQ ID NO: 12 at CDR1, CDR2, and CDR3 corresponding to amino acids 26 to 35, 51 to 65, and 96 to 107 of SEQ ID NO: 1, respectively.

[12] An affinity carrier comprising:
a solid phase carrier; and
an immunoglobulin-binding protein bound to the solid phase carrier,
wherein the immunoglobulin-binding protein comprises a polypeptide consisting of an amino acid sequence having an identity of at least 85% to an amino acid sequence of SEQ ID NO: 1 in which at least at one position selected from the group consisting of amino acids 97, 100, and 102 of SEQ ID NO: 1 is histidine.

[13] The affinity carrier according to [12], wherein the amino acid sequence having an identity of at least 85% to the amino acid sequence of SEQ ID NO: 1 has amino acid sequences of SEQ ID NO: 10, SEQ ID NO: 11, and SEQ ID NO: 12 at CDR1, CDR2, and CDR3 corresponding to amino acids 26 to 35, 51 to 65, and 96 to 107 of SEQ ID NO: 1, respectively.

[14] The affinity carrier according to [12], wherein the immunoglobulin-binding protein comprises a polypeptide consisting of an amino acid sequence of any of SEQ ID NOs: 5, 6, 7 and 8.

[15] An affinity carrier comprising:
a solid phase carrier; and
an immunoglobulin-binding protein bound to the solid phase carrier,
wherein the immunoglobulin-binding protein comprises a polypeptide consisting of an amino acid sequence having an identity of at least 85% to an amino acid sequence of SEQ ID NO: 1 in which at least at one position selected from the group consisting of amino acids 43, 53, 64, 75, and 86 of SEQ ID NO: 1 is arginine.

[16] The affinity carrier according to [15], wherein the amino acid sequence having an identity of at least 85% to the amino acid sequence of SEQ ID NO: 1 has amino acid sequences of SEQ ID NO: 10, SEQ ID NO: 11, and SEQ ID NO: 12 at CDR1, CDR2, and CDR3 corresponding to amino acids 26 to 35, 51 to 65, and 96 to 107 of SEQ ID NO: 1, respectively.

[17] The affinity carrier according to [15], wherein the immunoglobulin-binding protein comprises a polypeptide consisting of an amino acid sequence of SEQ ID NO: 9.

[18] A method for isolating an immunoglobulin or a fragment thereof using the affinity carrier according to any one of [1] to [17].

Effects of the Invention

An affinity carrier of the present invention shows improved elution behavior or binding capacity of immunoglobulins as compared with a parent antibody. The affinity carrier of the present invention can enhance the production efficiency of immunoglobulins or fragments thereof.

DETAILED DESCRIPTION OF THE INVENTION

Figure 1:
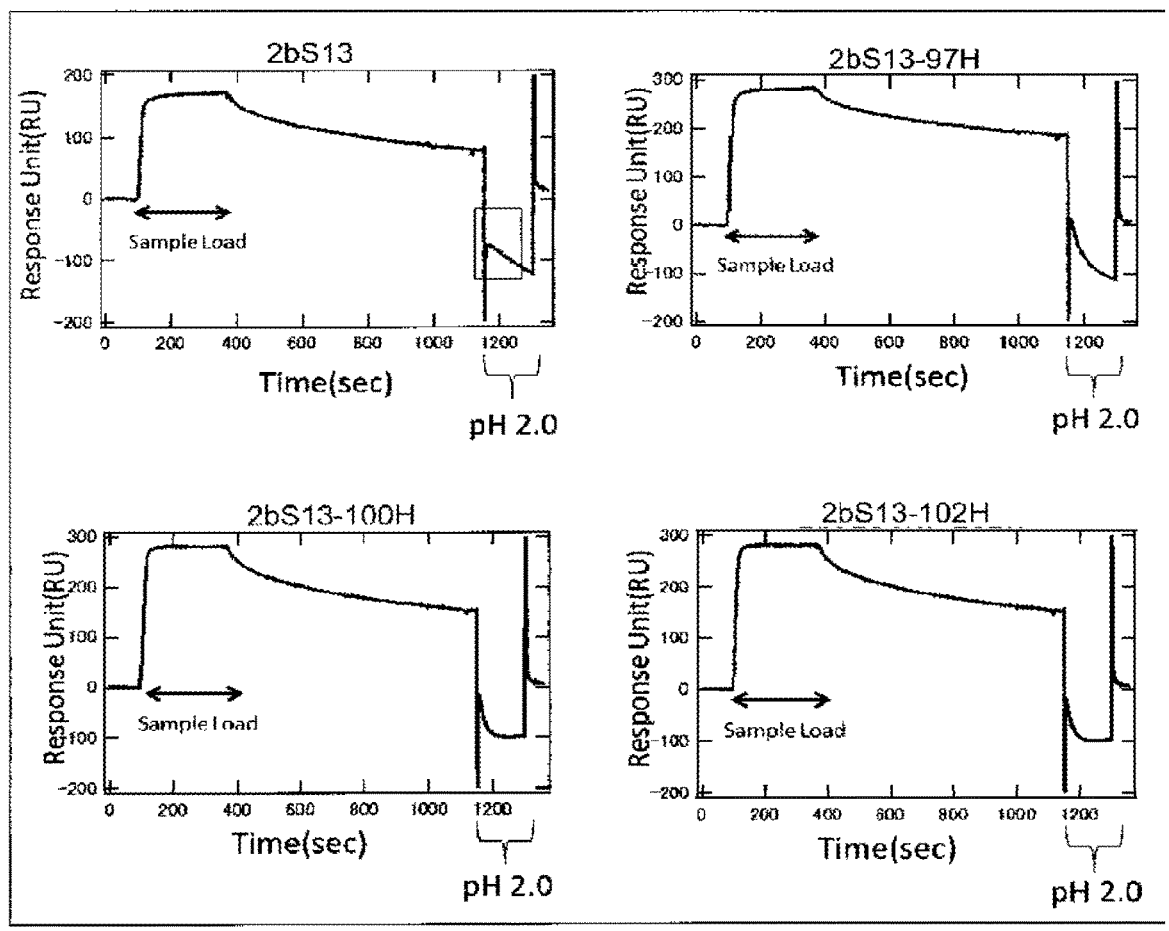
FIG. 1 illustrates the immunoglobulin association-dissociation behavior of a mutant VHH antibody of the present invention. The "pH 2.0" on the horizontal axis represents the time duration for flowing a pH 2.0 eluent.

The term "immunoglobulin-binding protein" herein refers to a protein having binding activity to an immunoglobulin or an immunoglobulin fragment. Examples of the term "immunoglobulin" (Ig) herein include immunoglobulins of any class such as IgG, IgA, IgD, IgE, IgM, and subclasses thereof. Examples of the immunoglobulin fragment herein include Fab, Fab', F(ab')$_2$, Fv, and other immunoglobulin fragments including a conjugate of immunoglobulin heavy and light chains having an antigen recognition site such as a reduced form of IgG (rIgG).

The term "antibody" herein refers to a molecule that specifically binds to a target such as a polynucleotide via at least one antigen recognition site in a variable domain of an immunoglobulin. Examples of the "antibody" herein include immunoglobulins of any class such as IgG, IgA, IgD, IgE, IgM, and subclasses thereof and also include fragments thereof (Fab, Fab', F(ab') 2, Fv, rIgG), single-chain antibodies (ScFv), heavy-chain antibodies, VHH (variable domain of heavy chain of heavy-chain antibodies), and mutants thereof. Furthermore, the "antibody" herein may be chimeric antibodies such as humanized antibodies, antibody conjugates, and other modified immunoglobulins having antigen recognition sites.

The term "VHH antibody" herein refers to an antibody comprising a variable domain of heavy chain of heavy-chain antibody (VHH) and is preferably a single domain antibody consisting of VHH. Heavy-chain antibodies have been found, for example, in camelids. The VHH antibody used in the present invention is preferably derived from a camelid. The VHH antibody used in the present invention may comprise a fragment of the constant domain of a heavy-chain antibody.

Examples of the camelids herein include *Camelus bactrianus*, *Camelus dromedarius*, *Lama glama*, *Vicugna pacos*, *Vicugna vicugna*, and *Lama guanicoe*. Among these examples, *Vicugna pacos* is preferable.

The term "antibody drug" herein refers to a drug comprising an antibody as the main component. Most antibodies contained in a drug as the main component are monoclonal antibodies. Rituximab (Rituxan (registered trademark)) serving as an anticancer agent, trastuzumab (Herceptin (registered trademark)), bevacizumab (Avastin (registered trademark)), infliximab (Remicade (registered trademark)) serving as an antirheumatic drug, adalimumab (Humira (registered trademark)), and ranibizumab (Lucentis (registered trademark)) serving as an angiogenesis inhibitor are examples of commercially available antibody drugs. However, the antibody drug referred to herein is not limited to these examples.

The term "epitope" herein refers to a site on an antigen that is recognized and bound by an antibody and interacts with the antibody.

According to the present specification, the identity of amino acid sequences or nucleotide sequences can be determined by using the algorithm BLAST (Pro. Natl. Acad. Sci. USA, 1993, 90:5873-5877) proposed by Karlin and Altschul. Based on this BLAST algorithm, programs called BLASTN, BLASTX, BLASTP, TBLASTN, and TBLASTX have been developed (J. Mol. Biol., 1990, 215:403-410). In a case in which these programs are used, the default parameters of the respective programs are used. Specific techniques of these analysis methods are known (see www.ncbi.nlm.nih.gov).

According to the present specification, the "identity of at least 85%" related to amino acid sequences and nucleotide sequences means an identity of 85% or higher, preferably an identity of 90% or higher, more preferably an identity of 95% or higher, even more preferably an identity of 978 or higher, still more preferably an identity of 98% or higher, and even more preferably an identity of 99% or higher. Furthermore, the "identity of at least 90%" related to amino acid sequences and nucleotide sequences means an identity of 908 or higher, preferably an identity of 95% or higher, more preferably an identity of 97% or higher, even more preferably an identity of 98% or higher, and still more preferably an identity of 99% or higher.

According to the present specification, a "corresponding position" on an amino acid sequence and a nucleotide sequence can be determined by subjecting a target sequence and a reference sequence (for example, an amino acid sequence set forth in SEQ ID NO: 9) to alignment so as to give the maximum homology to a conserved amino acid residue or nucleotide present in each amino acid sequence or nucleotide sequence. The alignment can be carried out using a known algorithm, and the procedure thereof is known to those ordinarily skilled in the art. For example, the alignment can be carried out using Clustal W Multiple Alignment Programs (Thompson, J. D. et al., 1994, Nucleic Acids Res., 22:4673-4680) with default settings. Clustal W can be utilized, for example, from the websites of European Bioinformatics Institute: EBI [www.ebi.ac.uk/index.html]) or the DNA Data Bank of Japan (DDBJ [www.ddbj.nig.ac.jp/Welcome-j.html]) operated by the National Institute of Genetics.

According to the present specification, amino acid residues may also be described by the following abbreviations: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), valine (Val or V); and an arbitrary amino acid residue (Xaa or X). Furthermore, according to the present specification, the amino acid sequence of a peptide is described according to a conventional method such that the amino terminal (hereinafter, referred to as N-terminal) is positioned on the left-hand side, and the carboxyl terminal (hereinafter, referred to as C-terminal) is positioned on the right-hand side.

The affinity carrier provided by the present invention comprises a solid phase carrier and an immunoglobulin-binding protein bound to the solid phase carrier. The immunoglobulin-binding protein included in the affinity carrier of the present invention comprises one or more mutant VHH antibodies or fragments thereof, preferably, one or more mutant VHH antibodies. When the immunoglobulin-binding protein comprises two or more mutant VHH antibodies or fragments thereof, the mutants or fragments thereof are preferably linked to each other directly or via a linker peptide. In an embodiment, the immunoglobulin-binding protein is essentially comprised of one or more mutant VHH antibodies or fragments thereof. In another embodiment, the immunoglobulin-binding protein is essentially comprised of one or more mutant VHH antibodies or fragments thereof, and a linker peptide.

Each mutant VHH antibody or each fragment thereof included in the affinity carrier of the present invention specifically binds to an epitope in a Fab domain of an immunoglobulin. The binding properties of the mutant VHH antibodies or fragments thereof differ from the binding properties of a domain in Protein A which binds to the Fc domain of an immunoglobulin and has been commonly used as a ligand in the related art. Therefore, affinity purification using the mutant VHH antibodies or fragments thereof enables isolation of not only a complete antibody molecule having the Fc domain but also a fragmented antibody such as Fab.

The mutant VHH antibodies or fragments thereof used in the present invention recognizes an epitope in at least one region selected from the group consisting of amino acids 127 to 184 of SEQ ID NO: 22 and amino acids 13 to 210 of SEQ ID NO: 23 but preferably epitopes in both regions. These epitope regions respectively correspond to regions within the light chain (SEQ ID NO: 22) and the heavy chain (SEQ ID NO: 23) of a Fab domain of trastuzumab. More specifically, the epitope recognized by the mutant VHH antibodies or fragments thereof is at least at one site selected from the group consisting of amino acids 127 to 129, 157 to 158, 180 to 182, and 184 of SEQ ID NO: 22 and amino acids 13, 119 to 125, 150 and 151, 153, 177 to 182, and 210 of SEQ ID NO: 23, preferably at a plurality of those sites, and more preferably at all of those sites A pre-mutation VHH antibody, or the source of the mutant VHH antibody used in the present invention, may hereinafter be referred to as "parent VHH antibody." Examples of the parent VHH antibody of the mutant VHH antibody of the present invention include a VHH antibody derived from a wild-type heavy-chain antibody (also referred to as "wild-type VHH antibody") and a mutation thereof having the same antigen-binding property as the wild-type VHH antibody.

Preferred examples of the parent VHH antibody include polypeptides consisting of any of the amino acid sequences of SEQ ID NOS: 1, 2, 3 and 4. SEQ ID NOs: 1, 2, 3 and 4 represent amino acid sequences of camelid-derived wild-type VHH antibodies having an affinity for a Fab domain of trastuzumab. Accordingly, another example of the parent VHH antibody of the mutant of the present invention includes a polypeptide consisting of an amino acid sequence having an identity of at least 85% to any of the amino acid sequences of SEQ ID NOS: 1, 2, 3 and 4 and having an affinity for a Fab domain of trastuzumab. More preferably, the parent VHH antibody is a polypeptide consisting of an amino acid sequence having an identity of at least 858 to the amino acid sequence of SEQ ID NO: 1 and having an affinity for a Fab domain of trastuzumab. The parent VHH antibody is preferably a camelid-derived VHH antibody. Accordingly, the mutant VHH antibody used in the present invention is preferably a camelid-derived mutant VHH antibody.

The parent VHH antibody consisting of the amino acid sequences of SEQ ID NOs: 1, 2, 3 and 4 comprises three complementarity-determining regions (CDRs) CDR1 to 3 in the amino acid sequences:

a VHH antibody with SEQ ID NO: 1 comprises CDR1, CDR2, and CDR3 consisting of amino acid sequences of SEQ ID NO: 10, SEQ ID NO: 11, and SEQ ID NO: 12 at amino acids 26 to 35, 51 to 65, and 96 to 107 of SEQ ID NO: 1, respectively;

a VHH antibody with SEQ ID NO: 2 comprises CDR1, CDR2, and CDR3 consisting of amino acid sequences of SEQ ID NO: 13, SEQ ID NO: 14, and SEQ ID NO: 15 at amino acids 26 to 37, 53 to 68, and 99 to 118 of SEQ ID NO: 2, respectively;

a VHH antibody with SEQ ID NO: 3 comprises CDR1, CDR2, and CDR3 consisting of amino acid sequences of SEQ ID NO: 16, SEQ ID NO: 17, and SEQ ID NO: 18 at amino acids 26 to 35, 51 to 66, and 97 to 116 of SEQ ID NO: 3, respectively; and a VHH antibody with SEQ ID NO: 4 comprises CDR1, CDR2, and CDR3 consisting of amino acid sequences of SEQ ID NO: 19, SEQ ID NO: 20, and SEQ ID NO:

21 at amino acids 26 to 35, 51 to 66, and 97 to 116 of SEQ ID NO: 4, respectively.

The parent VHH antibody which is a polypeptide consisting of an amino acid sequence having an identity of at least 85% to any of the amino acid sequences of SEQ ID NOS: 1, 2, 3 and 4 and having an affinity for a Fab domain of trastuzumab preferably comprises complementarity-determining regions CDR1 to CDR3 equivalent to those of the parent VHH antibody with SEQ ID NOS: 1, 2, 3 and 4:

a polypeptide consisting of an identity of at least 85% to the amino acid sequence of SEQ ID NO: 1 and having an affinity for a Fab domain of trastuzumab preferably comprises CDR1, CDR2, and CDR3 having amino acid sequences of SEQ ID NO: 10, SEQ ID NO: 11, and SEQ ID NO: 12 at regions corresponding to amino acids 26 to 35, 51 to 65, and 96 to 107 of SEQ ID NO: 1, respectively;

a polypeptide consisting of an identity of at least 85% to the amino acid sequence of SEQ ID NO: 2 and having an affinity for a Fab domain of trastuzumab preferably comprises CDR1, CDR2, and CDR3 having amino acid sequences of SEQ ID NO: 13, SEQ ID NO: 14, and SEQ ID NO: 15 at regions corresponding to amino acids 26 to 37, 53 to 68, and 99 to 118 of SEQ ID NO: 2, respectively;

a polypeptide consisting of an identity of at least 85% to the amino acid sequence of SEQ ID NO: 3 and having an affinity for a Fab domain of trastuzumab preferably comprises CDR1, CDR2, and CDR3 having amino acid sequences of SEQ ID NO: 16, SEQ ID NO: 17, and SEQ ID NO: 18 at regions corresponding to amino acids 26 to 35, 51 to 66, and 97 to 116 of SEQ ID NO: 3, respectively; and a polypeptide consisting of an identity of at least 85% to the amino acid sequence of SEQ ID NO: 4 and having an affinity for a Fab domain of trastuzumab preferably comprises CDR1, CDR2, and CDR3 having amino acid sequences of SEQ ID NO: 19, SEQ ID NO: 20, and SEQ ID NO: 21 at regions corresponding to amino acids 26 to 35, 51 to 66, and 97 to 116 of SEQ ID NO: 4, respectively.

The mutant VHH antibody used in the present invention is obtained by mutation of an amino acid residue of the parent VHH antibody. In an embodiment, the mutant VHH antibody is obtained by inserting at least one His into a CDR of the parent VHH antibody or by substituting His for at least one amino acid residue at a CDR of the parent VHH antibody. The mutant VHH antibody thus obtained may hereinafter be referred to as "His mutant of the present invention." Preferably, the CDR of the parent VHH antibody subjected to His insertion or substitution is at least one selected from the group consisting of the aforementioned CDR1 to CDR3, more preferably CDR3.

In a preferred embodiment, the His mutant of the present invention is obtained by inserting at least one His into CDR3 of a polypeptide consisting of an amino acid sequence having an identity of at least 85% to the amino acid sequences of SEQ ID NOS: 1, 2, 3 and 4 and having an affinity for a Fab domain of trastuzumab or by substituting His for at least one amino acid residue in CDR3 of the polypeptide. In a more preferred embodiment, the His mutant of the present invention is obtained by substituting His for at least one amino acid residue in CDR3 of a polypeptide consisting of an amino acid sequence having an identity of at least 858 to the amino acid sequence of SEQ ID NO: 1 and having an affinity for a Fab domain of trastuzumab. In a more preferred embodiment, the His mutant of the present invention is obtained by substituting His for at least one amino acid residue in CDR3 of a polypeptide consisting of an amino acid sequence having an identity of at least 85% to the amino acid sequence of SEQ ID NO: 1 and having an affinity for a Fab domain of trastuzumab at least at one position selected from the group consisting of positions corresponding to amino acids 97, 100, and 102 of SEQ ID NO: 1. Preferably, the amino acid residue to be substituted with His is an amino acid residue at positions corresponding to amino acids 97, 100, or 102 of SEQ ID NO: 1 or an amino acid residue at positions corresponding to amino acids 100 and 102 of SEQ ID NO: 1.

The His mutant thus obtained of the present invention has a CDR having at least one His inserted into the parent VHH antibody or having His substituted for at least one amino acid residue. Preferably, the His mutant of the present invention comprises CDR3 having at least one His inserted into the parent VHH antibody or having His substituted for at least one amino acid residue. More preferably, the His mutant of the present invention comprises CDR3 having His substituted for at least one amino acid residue of the parent VHH antibody. The His mutant of the present invention preferably has a CDR having the same amino acid sequence as the parent VHH antibody provided that His is inserted or substituted. The parent VHH antibody is preferably a polypeptide consisting of an amino acid sequence having an identity of at least 85% to the amino acid sequence of SEQ ID NO: 1 and having an affinity for a Fab domain of trastuzumab.

In a preferred embodiment, the His mutant of the present invention consists of an amino acid sequence having an identity of at least 85% to the amino acid sequence of SEQ ID NO: 1 and having His at least at one position selected from the group consisting of positions corresponding to amino acids 97, 100, and 102 of SEQ ID NO: 1. More preferably, the His mutant of the present invention has an amino acid sequence having an identity of at least 85% to the amino acid sequence of SEQ ID NO: 1 and comprises CDR1, CDR2, and CDR3 consisting of amino acid sequences of SEQ ID NO: 10, SEQ ID NO: 11, and SEQ ID NO: 12 at regions corresponding to amino acids 26 to 35, 51 to 65, and 96 to 107 of SEQ ID NO: 1, respectively, provided that, the His mutant of the present invention has His at least at one position selected from the group consisting of amino acids 97, 100, and 102 of SEQ ID NO: 1. More preferably, the His mutant of the present invention consists of the amino acid sequence of SEQ ID NO: 1 having His at positions corresponding to amino acid 97, 100, or 102, or 100 and 102 of SEQ ID NO: 1. The identity of the amino acid sequence of the His mutant and the amino acid sequence of SEQ ID NO: 1 is preferably 90% or more, more preferably 95% or more, still more preferably 97% or more, still more preferably 98% or more, and still more preferably 99% or more.

Preferred examples of the His mutant of the present invention include polypeptides having amino acid sequences of SEQ ID NOS: 5, 6, 7 and 8.

The His mutant of the present invention recognizes an epitope recognized by the mutant VHH antibody used in the present invention. Preferably, the His mutant of the present invention can bind to a Fab domain of trastuzumab.

In another embodiment, the mutant VHH antibody used in the present invention is obtained by substituting Arg for at least one Lys in the amino acid sequence of the parent VHH antibody. The mutant VHH antibody thus obtained may hereinafter be referred to as "Arg mutant of the present invention."

In a preferred embodiment, the Arg mutant of the present invention is obtained by substituting Arg for at least one Lys in an amino acid sequence of a polypeptide consisting of an amino acid sequence having an identity of at least 85% to the amino acid sequences of SEQ ID NOS: 1, 2, 3 and 4 and having an affinity for a Fab domain of trastuzumab. In a more preferred embodiment, the Arg mutant of the present invention is obtained by substituting Arg for at least one Lys in an amino acid sequence of a polypeptide consisting of an amino acid sequence having an identity of at least 85% to the amino acid sequence of SEQ ID NO: 1 and having an affinity for a Fab domain of trastuzumab at least at one position selected from the group consisting of positions corresponding to amino acids 43, 53, 64, 75, and 86 of SEQ ID NO: 1. Preferably, Arg is substituted for Lys at positions corresponding to amino acids 43, 53, 64, 75 and 86 of SEQ ID NO: 1.

The Arg mutant of the present invention thus obtained consists of an amino acid sequence in which Arg is substituted for at least one Lys in the amino acid sequence of the parent VHH antibody. The Arg mutant of the present invention preferably has a CDR having the same amino acid sequence as the parent VHH antibody provided that Arg is substituted. The parent VHH antibody is preferably a polypeptide consisting of an amino acid sequence having an identity of at least 85% to the amino acid sequence of SEQ ID NO: 1 and having an affinity for a Fab domain of trastuzumab.

In a preferred embodiment, the Arg mutant of the present invention consists of an amino acid sequence having an identity of at least 85% to the amino acid sequence of SEQ ID NO: 1 and has Arg at least at one position selected from the group consisting of positions corresponding to amino acids 43, 53, 64, 75, and 86 of SEQ ID NO: 1. More preferably, the Arg mutant of the present invention consists of an amino acid sequence having an identity of at least 85% to the amino acid sequence of SEQ ID NO: 1 and comprises CDR1, CDR2, and CDR3 consisting of amino acid sequences of SEQ ID NO: 10, SEQ ID NO: 11, and SEQ ID NO: 12 at regions corresponding to amino acids 26 to 35, 51 to 65, and 96 to 107 of SEQ ID NO: 1, respectively, provided that the Arg mutant of the present invention has Arg at least at one position selected from the group consisting of amino acids 43, 53, 64, 75, and 86 of SEQ ID NO: 1. Still more preferably, the Arg mutant of the present invention consists of the amino acid sequence of SEQ ID NO: 1 and has Arg at positions corresponding to amino acids 43, 53, 64, 75, and 86 of SEQ ID NO: 1. The identity between the amino acid sequence of the Arg mutant and the amino acid sequence of SEQ ID NO: 1 is preferably 90% or more, more preferably 95% or more.

A preferred example of the Arg mutant of the present invention includes a polypeptide consisting of an amino acid sequence of SEQ ID NO: 9.

The Arg mutant of the present invention recognizes an epitope recognized by the mutant VHH antibody used in the present invention. The Arg mutant of the present invention preferably binds to a Fab domain of trastuzumab.

In a further embodiment, the mutant VHH antibody used in the present invention is obtained by substituting another amino acid residue for Ser at a position corresponding to amino acid 84 of SEQ ID NO: 1 in an amino acid sequence of a polypeptide consisting of an amino acid sequence having an identity of at least 85% to the amino acid sequence of SEQ ID NO: 1 and having an affinity for a Fab domain of trastuzumab. The mutant VHH antibody thus obtained may hereinafter be referred to as "S84X mutant of the present invention." The amino acid residue substituted for Ser at the position corresponding to amino acid 84 is preferably Ala, Val, or Thr.

The S84X mutant of the present invention thus obtained consists of an amino acid sequence having an identity of at least 85% to the amino acid sequence of SEQ ID NO: 1 and having Ala, Val, or Thr at the position corresponding to amino acid 84 of SEQ ID NO: 1. More preferably, the S84X mutant of the present invention consists of an amino acid sequence having an identity of at least 85% to the amino acid sequence of SEQ ID NO: 1 and comprises CDR1, CDR2, and CDR3 consisting of amino acid sequences of SEQ ID NO: 10, SEQ ID NO: 11, and SEQ ID NO: 12 at regions corresponding to amino acids 26 to 35, 51 to 65, and 96 to 107 of SEQ ID NO: 1, respectively. However, the S84X mutant of the present invention has Ala, Val, or Thr at the position corresponding to amino acid 84 of SEQ ID NO: 1. The identity of the amino acid sequence of the S84X mutant and the amino acid sequence of SEQ ID NO: 1 is preferably 90% or more, more preferably 95% or more, still more preferably 97% or more, still more preferably 98% or more, and still more preferably 99% or more.

The S84X mutant of the present invention recognizes an epitope recognized by the mutant VHH antibody used in the present invention. Preferably, the S84X mutant of the present invention can bind to a Fab domain of trastuzumab.

The mutant VHH antibody used in the present invention may be the His mutant of the present invention, the Arg mutant of the present invention, the S84X mutant of the present invention, or a multiple mutant combining these mutations. Preferably, the multiple mutant is both the His mutant and the Arg mutant. In any case, the mutant VHH antibody recognizes the aforementioned epitope and preferably binds to a Fab domain of trastuzumab.

A fragment of the mutant VHH antibody used in the present invention may be a fragment of the His mutant of the present invention, a fragment of the Arg mutant of the present invention, a fragment of the S84X mutant of the present invention, or a fragment of a multiple mutant thereof. A fragment of the mutant VHH antibody used in the present invention recognizes an epitope recognized by the mutant VHH antibody used in the present invention and preferably binds to a Fab domain of trastuzumab.

The mutant VHH antibody or a fragment thereof used in the present invention is produced by techniques known in the related art such as chemical synthesis based on an amino acid sequence and recombinant technology. For example, the mutant VHH antibody or a fragment thereof is obtained by the following procedures. That is, a polynucleotide (such as DNA) that encodes the mutant or a fragment thereof is incorporated into a vector, and this vector is used to transform a host cell, and then, the resulting transformant is incubated in a medium to collect an expressed antibody or a fragment thereof. The polynucleotide that encodes the mutant VHH antibody or a fragment thereof is obtained by introduction of mutation into a polynucleotide that encodes the parent VHH antibody to cause the aforementioned His insertion, His substitution, or Arg substitution in a polypeptide to be encoded. Specific examples of a method for introducing mutation into a polynucleotide include site-directed mutagenesis, homologous recombination, and splicing by overlap extension (SOE)-PCR (Gene, 1989, 77:61-68). Detailed procedures for introducing mutation into a polynucleotide are well known to those skilled in the art.

Examples of the host used for the transformation include bacteria such as *Escherichia coli*, and microorganisms such as yeasts and fungi. Among these examples, *Escherichia coli* is preferable. Any known vector (such as a plasmid) that replicates itself in a host cell may be employed as the vector for the transformation, and a preferred example is an expression vector. The expression vector may be any known vector that replicates itself in a host cell such as a plasmid disclosed in U.S. Pat. No. 5,151,350 or a plasmid disclosed in Molecular Cloning edited by Sambrook et al. (Cold Spring Harbor Laboratory Press, 3rd edition, 2001). Depending on hosts, the transformation may employ any technique known in the related art such as a method disclosed in Molecular Cloning edited by Sambrook et al. (Cold Spring Harbor Laboratory Press, 3rd edition, 2001). The method for incubating the obtained transformant (such as a microbial cell) to collect an expressed protein is well known to those skilled in the art. Alternatively, the mutant VHH antibody or a fragment thereof may be expressed using a cell-free protein synthesis system.

When an immunoglobulin-binding protein containing two or more mutant VHH antibodies or fragments thereof is produced as the immunoglobulin-binding protein used in the affinity carrier of the present invention, a polynucleotide having two or more of the mutant VHH antibodies or fragments thereof linked to each other is produced, and the polynucleotide is incorporated into a vector, and this vector is used to transform a host cell, and then, the resulting transformant is incubated to collect an expressed target protein as in the aforementioned procedures.

Accordingly, the present invention also provides a polynucleotide that encodes the mutant VHH antibody used in the present invention, a vector comprising the same, and a transformant comprising the polynucleotide or the vector.

An immunoglobulin-binding protein comprising the mutant VHH antibody or a fragment thereof can be used as an affinity ligand. The affinity carrier of the present invention is produced by immobilizing the immunoglobulin-binding protein of the present invention on a solid phase carrier. The solid phase carrier used for the affinity carrier of the present invention is preferably an insoluble carrier. Preferably, the affinity carrier of the present invention is a carrier for affinity chromatography.

Examples of the solid phase carrier include organic supports such as synthetic polymer supports or natural polymer supports; inorganic supports; and organic-organic composite supports or organic-inorganic composite supports combining the aforementioned supports. Examples of the synthetic polymer supports include those comprising polyvinyl alcohols, poly(meth)acrylates, poly(meth)acrylamides, polystyrenes, and ethylene-maleic anhydride copolymers. Examples of the natural polymer supports include those comprising polysaccharides such as agarose, dextran, mannan, and cellulose. Alternatively, the natural polymer supports may be physically cross-linked polysaccharides or chemically cross-linked polysaccharides. Examples of the inorganic supports include those comprising glass beads, silica gel, metals, and metal oxides. Among these examples, synthetic polymer supports are preferable from a viewpoint of flow-rate characteristics. The affinity carrier of the present invention has sufficient antifouling property even when a synthetic polymer support is used as a support. A preferred example of the synthetic polymer support is a copolymer of a monofunctional unsaturated monomer and a polyfunctional unsaturated monomer, and a preferred example of the monofunctional unsaturated monomer is a monofunctional unsaturated monomer having an epoxy group or a ring-opening epoxy group. An amount of the polyfunctional unsaturated monomer used is usually 1 to 100 parts by mass, and preferably 1 to 50 parts by mass, based on 100 parts by mass of the monofunctional unsaturated monomer.

The support may be non-porous or porous but is preferably porous. The support may have any aspect of, for example, particle, monolith, plate, chip, fiber, or membrane (including hollow fiber membrane). However, from a viewpoint of capturing a target substance, the support preferably has an aspect of particle, monolith, plate, fiber, or membrane, and more preferably, an aspect of particle.

In a case where the support is a particle, the support preferably has a particle size of 30 µm or more from a viewpoint of flow-rate characteristics and preferably has a particle size of 300 µm or less from a viewpoint of capturing a target substance. Such particle sizes are adjustable by polymerization conditions or classification. The "particle size" in the present invention represents a volume average particle size obtained by a laser diffraction/scattering particle size distribution analyzer.

In a case where the support is a porous particle, when pore sizes in a range of 10 nm to 5000 nm are measured, a specific surface area of the support is preferably 70 $m^2/g$ or more, and more preferably 90 $m^2/g$ or more. The "specific surface area" in the present invention is a value obtained by dividing the surface area of a pore having a pore diameter of 10 to 5000 nm obtained with a mercury porosimeter by the dry mass of a particle.

The support may employ a commercially available product or one synthesized according to a method in the related art. For example, the synthetic polymer support can be obtained according to known methods disclosed, for example, in JP 58-058026 B and JP 53-090991 A.

The method for binding a ligand (that is, the immunoglobulin binding protein of the present invention) to the solid-phase support, can be carried out using a general method of immobilizing a protein on a support. Examples include a method of using a support having a carboxy group, activating this carboxy group by means of N-hydroxysuccinic acid imide, and reacting the carboxy group with an amino group of a ligand; a method of using a support having an amino group or a carboxy group, reacting the support with a carboxy group or an amino group of a ligand in the presence of a dehydration condensing agent such as a water-soluble carbodiimide, and thereby forming an amide bond; a method of using a support having a hydroxyl group, activating the support with a cyan halide such as cyan bromide, and reacting the support with an amino group of a ligand; a method of tosylating or tresylating a hydroxyl group of a support, and reacting the hydroxyl group with an amino group of a ligand; a method of introducing an epoxy group into a support by means of, for example, bisepoxide or epichlorohydrin, and reacting the support with an amino group, a hydroxyl group, or a thiol group of a ligand; and a method of using a support having an epoxy group, and reacting the support with an amino group, a hydroxy group, or a thiol group of a ligand. Among the methods described above, from the viewpoint of the stability in an aqueous solution to be subjected to a reaction, a method of binding a ligand via an epoxy group is desirable.

A hydroxyl group, which is a ring-opening epoxy group produced by ring-opening of an epoxy group, hydrophilizes a support surface and prevents non-specific adsorption of a protein for example, also enhances the toughness of a support in water, and thus accomplishes the role of preventing the destruction of the support at a high flow rate. Therefore, in a case in which residual epoxy groups that are not bound to the ligand exist in the support after having the ligand immobilized thereon, it is preferable to ring-open these residual epoxy groups. Regarding the method of ring-opening epoxy groups in the support, for example, a method of stirring the support with an acid or an alkali under heating or at room temperature in an aqueous solvent may be mentioned. Furthermore, epoxy groups may also be ring-opened with a blocking agent having a mercapto group, such as mercaptoethanol or thioglycerol, or with a blocking agent having an amino group, such as monoethanolamine. A more preferred ring-opened epoxy group is a ring-opened epoxy group obtainable by ring-opening an epoxy group contained in the support by means of thioglycerol. Thioglycerol has low toxicity even compared to, for example, mercaptoethanol as a raw material, and an epoxy ring-opened group having thioglycerol added thereto has an advantage that the non-specific adsorption occurs at a lower level than a ring-opened group obtained by a blocking agent having an amino group and that the dynamic binding amount is high.

If necessary, a molecule having an arbitrary length (spacer) may be introduced between a solid-phase support and a ligand. Examples of the spacer include a polymethylene chain, a polyethylene glycol chain, and saccharides.

The affinity carrier of the present invention isolates not only a complete immunoglobulin molecule but also a fragmented antibody such as Fab. Therefore, the present invention further provides a method for isolating an immunoglobulin or a fragment thereof using the affinity carrier of the present invention. The immunoglobulin or a fragment thereof isolated in the present invention is preferably an antibody. More preferable examples of the immunoglobulin or a fragment thereof include immunoglobulins of any class such as IgG, IgA, IgD, IgE, IgM, and subclasses thereof and also include fragments thereof (such as Fab, Fab', $F(ab')_2$, and rIgG).

Hereinafter described is a method for isolating an immunoglobulin or a fragment thereof according to an embodiment of the present invention. The method for isolating an immunoglobulin or a fragment thereof according to the present embodiment preferably involves dipping of a specimen containing a target substance (an immunoglobulin or a fragment thereof) in an affinity carrier comprising an immobilized ligand (an immunoglobulin-binding protein comprising the mutant VHH antibody or a fragment thereof) to cause the carrier to absorb the target substance (first step), and eluting of the target substance from the carrier (second step).

In the first step, the specimen containing the target substance is flown through, for example, a column loaded with the affinity carrier of the present invention under the condition that the ligand absorbs the target substance. In this first step, most substances other than the target substance in the specimen pass through the column without being adsorbed by the ligand. If necessary, the carrier may be washed with neutral buffer containing a salt such as NaCl in order to remove part of substances weakly retained by the ligand.

In the second step, an acidic eluent is flown to elute the target substance adsorbed by the ligand. This eluate is collected so as to isolate the desired immunoglobulin or a fragment thereof from the specimen. The pH of the eluent is preferably 2 or higher, more preferably 2.5 or higher, still more preferably 3 or higher, but preferably 5 or lower, more preferably 4.5 or lower, and still more preferably 4 or lower. For example, the pH of the eluent is preferably 2 to 5, more preferably 2 to 4.5, still more preferably 2 to 4, still more preferably 2.5 to 5, still more preferably 2.5 to 4.5, still more preferably 2.5 to 4, still more preferably 3 to 5, still more preferably 3 to 4.5, and still more preferably 3 to 4.

In an embodiment of the method for isolating an immunoglobulin or a fragment thereof according to the present invention, the isolated immunoglobulin or a fragment thereof is used as an antibody drug. Therefore, an embodiment of the present invention provides a method for producing an antibody drug using the affinity carrier of the present invention. The procedures of the method are basically the same as the procedures of the method for isolating an immunoglobulin or a fragment thereof except for using a specimen containing the desired immunoglobulin or a fragment thereof to be used for an antibody drug.

EXAMPLES

Hereinafter, the present invention will be described more specifically with reference to Examples. The following description generally illustrates embodiments of the present invention, and the present invention is not limited to the description by no particular reason.

Reference Example 1. Synthesis of Porous Particles (1) To 360 g of pure water, 3.58 g of polyvinyl alcohol (PVA-217 available from Kuraray Co., Ltd.) was added, and the polyvinyl alcohol was dissolved by heating and stirring. After the resultant is cooled, 0.36 g of sodium dodecyl sulfate (available from FUJIFILM Wako Pure Chemical Corporation), 0.36 g of sodium sulfate (available from FUJIFILM Wako Pure Chemical Corporation), and 0.18 g of sodium nitrite (available from FUJIFILM Wako Pure Chemical Corporation) were added and stirred to prepare Aqueous solution S.

(2) A monomer composition consisting of 12.00 g of glycidyl methacrylate (available from Mitsubishi Chemical Corporation) and 1.33 g of divinylbenzene (available from Nippon Steel Chemical Co., Ltd.) was dissolved in 24.43 g of diisobutyl ketone (available from Mitsui Chemicals Co., Ltd.) to prepare a monomer solution.

(3) The total amount of Aqueous solution S was put into a 500 mL separable flask. The flask was fitted with a thermometer, a stirring blade, and a cooling tube and was set in a hot water bath. Then, Aqueous solution S was stirred under a nitrogen atmosphere. The total amount of the monomer solution was put into the separable flask and heated in the hot water bath. When the internal temperature reached 85° C., 0.53 g of 2,2'-azoisobutyronitrile (available from FUJIFILM Wako Pure Chemical Corporation) was added to the mixture.

(4) The resulting reaction solution was stirred for three hours while maintaining the temperature at 86° C. Then, the reaction solution was cooled, filtered, and washed with pure water and ethanol. The washed particles were dispersed in pure water and decanted three times to remove small particles. Then, the particles were dispersed in pure water to make the particles have a concentration of 10% by mass, whereby obtaining Dispersion liquid A.

(5) A composition consisting of 66.00 g of polyethylene glycol diglycidyl ether and 45.70 g of sodium sulfate (available from FUJIFILM Wako Pure Chemical Corporation) was mixed with 388.3 g of 0.1M carbonate buffer to prepare Aqueous solution E.

(6) Thioglycolic acid (available from FUJIFILM Wako Pure Chemical Corporation) in amount of 23.03 g and sodium sulfate (available from FUJIFILM Wako Pure Chemical Corporation) in amount of 7.10 g were dissolved in pure water, and then, sodium hydroxide (available from FUJIFILM Wako Pure Chemical Corporation) was added to prepare 500 mL of Aqueous solution C (pH 8.3).

(7) Aqueous solution E and Dispersion liquid A were subjected to suction filtration, and the filtrate thus obtained was put in a 1 L plastic bottle. The bottle was set in a rotor stirrer to stir the filtrate at room temperature. After two hours, the resulting liquid was filtered and washed with pure water.

(8) The filtrate (17.00 g) and the total amount of Aqueous solution C were put in a 1 L plastic bottle. The bottle was set in the rotor stirrer to stir the mixture at room temperature. After four hours, the resulting liquid was filtered and washed with pure water and 16 vol % ethanol. Then, the particles were dispersed in 16 vol % ethanol to make the particles have a particle volume of 50% (v/v), whereby yielding a liquid in which porous particles (PB) were dispersed.

Example 1. Production of VHH Antibody (1) Production of VHH antibody 2bS13:

Prepared was a plasmid that codes a VHH antibody 2bS13 derived from a camelid wild-type heavy-chain antibody and a PB-immobilizing linker peptide linked to C terminus of the VHH antibody 2bS13. The VHH antibody 2bS13 consists of an amino acid sequence of SEQ ID NO: 1 and binds to trastuzumab (Herceptin (registered trademark)). This plasmid was used to transform *Escherichia coli* competent cells BL21 (DE3) (available from New England Biolabs). The resulting transformants were incubated at 37° C. until the absorbance (OD600) reached about 10, and then, IPTG (available from FUJIFILM Wako Pure Chemical Corporation) was added to make the final concentration 1 mM. The transformants were further incubated at 37° C. for five hours so as to express a recombinant VHH antibody protein. After the protein expression, the cells were collected by centrifugation, dispersed in Tris buffer of pH 8.5, and disrupted with a homogenizer. The obtained cell-disrupted solids were dispersed in a solution containing a denaturing agent of guanidine hydrochloride (FUJIFILM Wako Pure Chemical Corporation), and 2bS13 was purified by BioPro S and BioPro Q (YMC Inc.). The purified protein was refolded by multiple dialysis against 20 mM phosphate buffer.

(2) Production of his Substituted Mutant VHH Antibody:

A mutant VHH antibody having His substituted for an amino acid residue of CDR3 of 2bS13 was produced. Prepared were a plasmid that encodes a mutant VHH antibody 2bS13-97H having His substituted for amino acid 97 of SEQ ID NO: 1, a plasmid that encodes a mutant VHH antibody 2bS13-100H having His substituted for amino acid 100 of SEQ ID NO: 1, a plasmid that encodes a mutant VHH antibody 2bS13-102H having His substituted for amino acid 102 of SEQ ID NO: 1, and a plasmid that encodes a mutant VHH antibody 2bS13-100-102H having His substituted for amino acids 100 and 102 of SEQ ID NO: 1. Using these plasmids, mutant VHH antibody proteins 2bS13-97H (SEQ ID NO: 5), 2bS13-100H (SEQ ID NO: 6), 2bS13-102H (SEQ ID NO: 7), and 2bS13-100-102H (SEQ ID NO: 8) each having His substitution in CDR3 were prepared in a similar manner to (1).

(3) Production of Arg Substituted Mutant VHH Antibody:

A mutant VHH antibody having Arg substituted for Lys in 2bS13 was produced. Prepared was a plasmid which encodes a mutant VHH antibody 2bS13-KR5 having Arg substituted for five Lys in the amino acid sequence of 2bS13 (that is, Lys in amino acids 43, 53, 64, 75, and 86 of SEQ ID NO: 1). Using this plasmid, a mutant VHH antibody protein 2bS13-KR5 (SEQ ID NO: 9) was prepared in a similar manner to (1).

Example 2. Preparation of Affinity Carrier

A monomer composition consisting of 0.22 g of N-hydroxysulfosuccinimide (available from FUJIFILM Wako Pure Chemical Corporation) and 0.95 g of 1-(3-dimethylaminopropyl)-3-ethylcarbodiimide hydrochloride (available from FUJIFILM Wako Pure Chemical Corporation) was dissolved in 1.84 g of 0.02M MES buffer (pH 5.5) to prepare a monomer solution. The monomer solution was mixed with 0.5 g of the porous particles (PB) obtained in Reference Example 1, set on a rotor stirrer, and stirred at room temperature. After 30 minutes, the resulting solution was filtered and washed with 0.02M MES buffer (pH 5.5) and sodium phosphate buffer (pH 7.5). The resulting filtrate and each of the VHH antibodies prepared in Example 1 were mixed with 0.02M sodium phosphate buffer (pH 7.5) so that 1 g of the porous particles contained 0.12 g of protein. The porous particles were shaken at 25° C. for five hours to immobilize the VHH antibodies on the porous particles, whereby yielding carriers for affinity chromatography using the VHH antibodies as a ligand (2bS13/PB, 2bS13-97H/PB, 2bS13-100H/PB, 2bS13-102H/PB, 2bS13-100-102H/PB, and 2bS13-KR5/PB). N-hydroxysulfosuccinimide groups remaining on these particles were blocked with tris(hydroxymethyl)aminomethane. The particles were then washed with 0.001M NaOH and 0.1M citrate buffer (pH 2.5) and suspended in PBS in the end.

Test Example 1. Identification of Antigenic Epitope of VHH Antibody

An epitope recognized by the VHH antibody prepared in Example 1 was examined.

(1) Obtaining Crystal of VHH Antibody-Trastuzumab Conjugate:

Trastuzumab (Herceptin (registered trademark)), a monoclonal antibody, was digested with papain to prepare Fab. The obtained trastuzumab Fab was mixed with the camelid wild-type heavy-chain antibody-derived VHH antibody 2bS13 (SEQ ID NO: 1), and a conjugate was fractionated by HPLC. Using the conjugate, the protein was crystallized by Gryphon, a protein crystallization dispensing system manufactured by Art Robbins Instruments, whereby obtaining a crystal of a conjugate comprising the VHH antibody 2bS13 and the trastuzumab Fab.

(2) Evaluation of Three-Dimensional Structure of VHH Antibody-Trastuzumab Conjugate:

The conjugate was modeled and refined based on X-ray diffraction data of the obtained crystal of the conjugate. In regard to models of the conjugate, the VHH antibody, and the trastuzumab Fab, calculations were performed to obtain changes in accessible surface area (hereinafter referred to as ASA) of each amino acid residue included in each protein. Table 1 shows residues at positions where the changes in ASA on amino acid sequences of the light chain (SEQ ID NO: 22) and the heavy chain (SEQ ID NO: 23) of the trastuzumab Fab were 1 or more. At positions where the changes in ASA are 1 or more, the VHH antibody and the trastuzumab Fab interact with each other, and the residues at such positions are regarded as epitopes. These results show that the VHH antibody is not an antibody like Protein A that binds to Fc domains but an antibody that recognizes Fab domains.

TABLE 1

| LIGHT CHAIN (SEQ ID NO: 22) | | | HEAVY CHAIN (SEQ ID NO: 23) | | |
|---|---|---|---|---|---|
| POSITION | RESIDUE | ASA CHANGE | POSITION | RESIDUE | ASA CHANGE |
| 127 | Ser | 30.0 | 13 | Gln | 33.2 |
| 128 | Gly | 17.6 | 119 | Ser | 12.3 |
| 129 | Thr | 33.6 | 120 | Ser | 4.8 |
| 157 | Gly | 18.9 | 121 | Ala | 25.3 |
| 158 | Asn | 17.5 | 122 | Ser | 80.2 |
| 180 | Thr | 42.2 | 123 | Thr | 33.2 |
| 181 | Leu | 4.1 | 124 | Lys | 69.0 |
| 182 | Ser | 38.7 | 125 | Gly | 8.1 |
| 184 | Ala | 7.1 | 150 | Lys | 17.2 |
| | | | 151 | Asp | 25.5 |
| | | | 153 | Phe | 18.8 |
| | | | 177 | Lau | 16.4 |
| | | | 178 | Gln | 2.7 |
| | | | 179 | Ser | 92.5 |
| | | | 180 | Ser | 73.6 |
| | | | 181 | Gly | 35.5 |
| | | | 182 | Leu | 33.8 |
| | | | 210 | Ser | 28.2 |

Test Example 2. Evaluation of Ig Association-Dissociation Behavior of his Substituted Mutant VHH Antibodies In regard to 2bS13, 2bS13-97H, 2bS13-100H, and 2bS13-102H prepared in Example 1, the Ig binding ability was evaluated with Biacore (manufactured by GE Healthcare). Those VHH antibodies were dispersed in HBS-EP (10 mM Hepes, 150 mM NaCl, 3 mM EDTA, and 0.005% Tween-20) to produce 12.5 to 150 nM VHH antibody solutions. The trastuzumab Fab prepared in Test Example 1 was immobilized on a Biacore sensor chip, and each VHH antibody solution was applied thereto. The measurements were performed under neutral conditions (pH 7.4). Curve fitting utilizing binding model was applied to association and dissociation behaviors, whereby evaluating the association rate constant ($K_{on}$), the dissociation rate constant ($K_{off}$), and the affinity (KD). Furthermore, this sensor chip was washed with an acidic eluent (10 mM Glycine-HCl+0.5M NaCl, pH 2.0) to measure a signal. From the obtained signal shape, the elution behavior of Ig by the acid was examined. The faster the signal attenuates immediately after washing the chip with the eluent, the easier the VHH antibody is released from the antibody-immobilized sensor chip under acidic conditions, which indicates that the VHH antibody has high Ig elution efficiency.

Table 2 and FIG. 1 show measurement results. Table 2 shows that each of the mutant VHH antibodies is equivalent to the parent antibody 2bS13 in KD with respect to the trastuzumab Fab under neutral conditions and that each of the mutant VHH antibodies have the Ig binding ability equivalent to that of the parent antibody. In addition, each of the mutant VHH antibodies has a higher signal attenuation rate than the parent antibody 2bS13 immediately after washing with the acidic eluent (see the area surrounded by a square in FIG. 1), which indicates that the mutant VHH antibodies enhanced in Ig elution behavior under acidic conditions compared to the parent antibody.

TABLE 2

| VHH ANTIBODY | $K_{on}$ (1/Ms) | $K_{off}$ (1/s) | KD (nM) | IgG ELUTION BEHAVIOR (COMPARED TO 2bS13) |
|---|---|---|---|---|
| 2bS13 | $3.25e^7$ | 0.0147 | 0.45 | — |
| 2bS13-97H | $1.97e^7$ | 0.0040 | 0.205 | IMPROVED |
| 2bS13-100H | $2.08e^7$ | 0.0078 | 0.376 | IMPROVED |
| 2bS13-102H | $1.58e^7$ | 0.0227 | 1.44 | IMPROVED |

Test Example 3. Ig Elution Ability of Affinity Carrier Using his Substituted Mutant VHH Antibodies Affinity chromatography was conducted using columns loaded with the affinity carriers 2bS13/PB, 2bS13-100H/PB, and 2bS13-100-102H/PB obtained in Example 2 to evaluate the Ig elution ability from the carriers under acidic conditions. All chromatographic experiments were performed with AKTA avant 150 (manufactured by GE Healthcare). In the chromatography, Tricorn 5/50 columns (available from GE Healthcare) were used, and the columns were loaded with the affinity carriers obtained in Example 2 (column volume 1 mL). The same trastuzumab Fab as in Test Example 1 was used as Ig to be bound to the carriers. Sodium citrate buffer of pH 7.5 was used as a loading solution, while sodium citrate buffer of pH 3.0 and sodium citrate buffer of pH 2.5 were sequentially used as eluents. An amount of Ig in each eluate was measured by sequentially monitoring OD280 of eluates from the columns. Among fractions eluted by the pH 3.0 eluent and the pH 2.5 eluent, the volume of a fraction having OD280 of 0.12 AU or more was examined.

Figure 2:
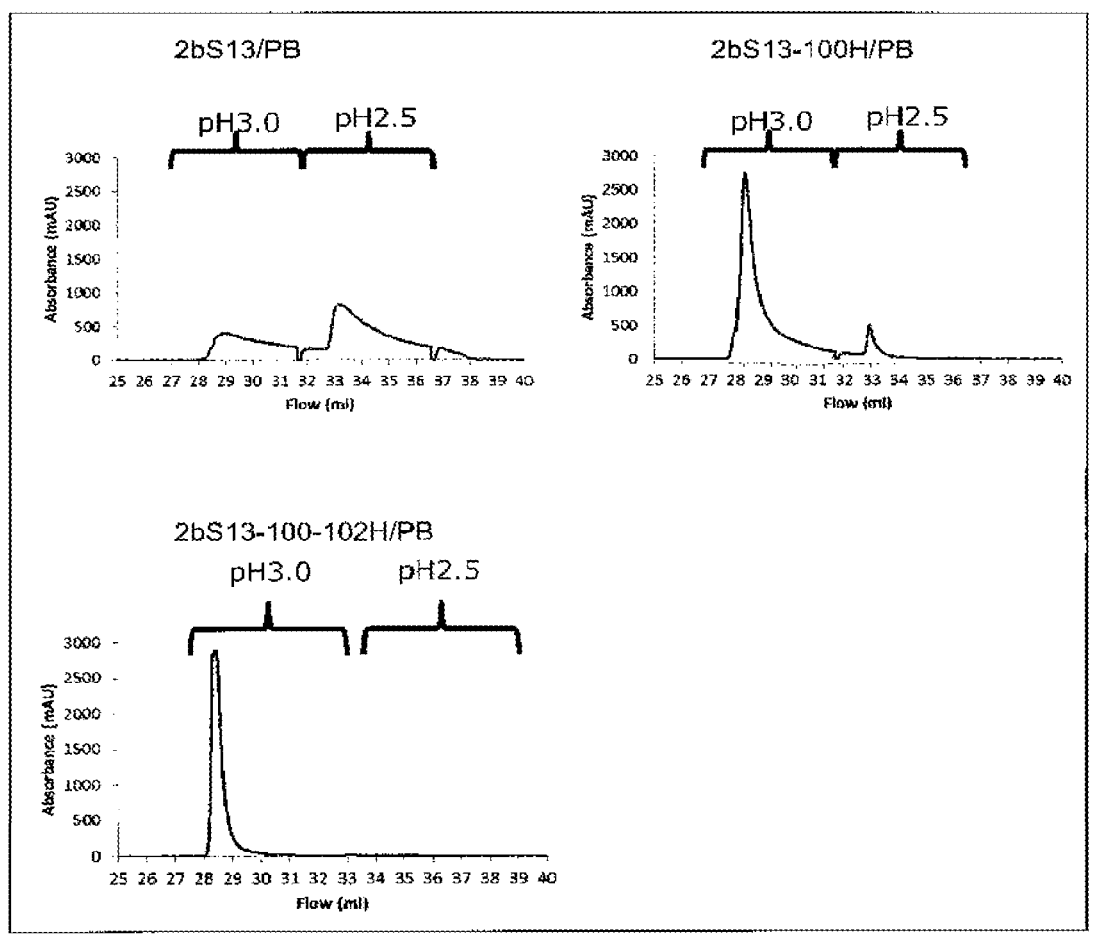
FIG. 2 illustrates the elution behavior of an immunoglobulin from an affinity carrier which comprises the mutant VHH antibody of the present invention as a ligand.

FIG. 2 shows changes in OD280 of the eluates from the columns. The carrier 2bS13/PB using a ligand without His substitution hardly eluted Ig at pH 3.0, and even when the pH was lowered to 2.5, the amount of Ig eluted was little. On the other hand, in the carrier 2bS13-100H/PB using a ligand with His substitution mutation, most of the binding Ig was eluted at pH 3.0. Furthermore, the carrier 2bS13-100-102H/PB using a double His substituted mutant eluted almost all the binding Ig at pH 3.0.

Table 3 shows amounts of eluent required to elute Ig bound to the carriers. The carrier using the ligand with His substitution mutation eluted a sufficient amount of Ig by the pH 3.0 eluent. The more the number of His substitutions on the ligand increased, the less the amount of eluent required for Ig elution. On the other hand, the carrier using the ligand without His substitution could not elute a sufficient amount of Ig even when using the eluent of pH 2.5 or more in large amounts.

TABLE 3

| | | AMOUNT OF ELUENT (column volume; CV) | |
|---|---|---|---|
| LIGAND | NUMBER OF His SUBSTITUTIONS | pH 3.0 | pH 2.5 |
| 2bS13 | 0 | >4 CV | >4 CV |
| 2bS13-100H | 1 | 3.7 CV | N/A |
| 2bS13-100-102H | 2 | 1.2 CV | N/A |

Test Example 4. Ig Binding Ability of Affinity Carrier Using Arg Substituted Mutant VHH Antibody (1) Measurement of Amount of Ligand Immobilized:

BCA protein assay was conducted using 1 mg of the affinity carriers prepared in Example 2 on which the VHH antibody 2bS13 or mutant 2bS13-KR5 was immobilized. An amount of ligand immobilized was determined based on the calibration curve.

(2) Measurement of Static Binding Capacity (SBC):

To 3 mg of a matrix prepared in (1) comprising the immobilized VHH antibody, added was 0.5 g of a trastuzumab Fab equivalent to one used in Test Example 1 dissolved in sodium phosphate buffer (pH 7.5), and the matrix was stirred at 25° C. with a shaker. After one hour, the solution was filtered and washed with sodium phosphate buffer (pH 7.5), and the washed solution was mixed with the filtrate. OD280 of the obtained aqueous solution was measured to determine an amount of Fab leaked. The amount of Fab leaked was subtracted from the initial amount of Fab added to calculate the static binding capacity (SBC).

Table 4 shows measurement results. The data in Table 4 shows the results of three measurements for each carrier and average values thereof.

TABLE 4

| VHH ANTI-BODY | NUMBER OF Arg SUBSTI-TUTIONS | AMOUNT OF LIGAND IMMOBILIZED [μg/mg-PARTICLE] | SBC [mg-Ig/mg-PARTICLE] |
|---|---|---|---|
| 2bS13 | — | 63 | 69 |
|  |  | 75 | 74 |
|  |  | 80 | 82 |
|  |  | AVERAGE 72.7 | AVERAGE 75 |
| 2bS13-KR5 | 5 | 79 | 100 |
|  |  | 78 | 101 |
|  |  | 84 | 110 |
|  |  | AVERAGE 80.3 | AVERAGE 103.7 |

The invention claimed is:

1. An affinity carrier, comprising:
a solid phase carrier; and
an immunoglobulin-binding protein bound to the solid phase carrier,
wherein the immunoglobulin-binding protein comprises a mutant VHH antibody, or a fragment thereof, comprising a polypeptide having at least 90% identity to the amino acid sequence of SEQ ID NO: 1, the polypeptide has the CDR1 and CDR2 amino acid sequences of SEQ ID NO: 10 and SEQ ID NO: 11, respectively, corresponding to amino acids 26 to 35 and 51 to 65 of SEQ ID NO: 1, the polypeptide has the CDR3 amino acid sequence of SEQ ID NO: 12 corresponding to amino acids 96 to 107 of SEQ ID NO: 1, in which at least at one position selected from the group consisting of amino acids 97, 100, and 102 of SEQ ID NO: 1 has been substituted with histidine, and the immunoglobulin-binding protein binds to an Fab domain of trastuzumab.

2. The affinity carrier according to claim 1, wherein the immunoglobulin-binding protein comprises a polypeptide selected from the group consisting of SEQ ID NOS: 5, 6, 7 and 8.

3. An affinity carrier, comprising:
a solid phase carrier; and
an immunoglobulin-binding protein bound to the solid phase carrier,
wherein the immunoglobulin-binding protein comprises a mutant VHH antibody, or a fragment thereof, comprising a polypeptide having at least 90% identity to the amino acid sequence of SEQ ID NO: 1, the polypeptide has at least one position selected from the group consisting of amino acids 43, 53, 64, 75, and 86 of SEQ ID NO: 1 substituted with arginine and retains the CDR1, CDR2, and CDR3 amino acid sequences of SEQ ID NO: 10, SEQ ID NO: 11, and SEQ ID NO: 12, respectively, corresponding to amino acids 26 to 35, 51-65, and 96-107 of SEQ ID NO: 1 except for any substitution at amino acid positions 53 and 64 in CDR2, and the immunoglobulin-binding protein binds to an Fab domain of trastuzumab.

4. The affinity carrier according to claim 3, wherein the immunoglobulin-binding protein comprises the polypeptide of SEQ ID NO: 9.

* * * * *

```
                      SEQUENCE LISTING

<160> NUMBER OF SEQ ID NOS: 23

<210> SEQ ID NO 1
<211> LENGTH: 118
<212> TYPE: PRT
<213> ORGANISM: Vicugna pacos
<220> FEATURE:
<223> OTHER INFORMATION: VHH antibody 2bS13

<400> SEQUENCE: 1

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Ser Phe Ala Ile Asn
            20                  25                  30

Asn Val Ala Trp Tyr Arg Gln Ala Pro Gly Lys Gln Arg Asp Leu Val
        35                  40                  45

Ala Leu Ile Asp Lys Tyr Asp Thr Gly Asn Ile Ala Asp Ser Val Lys
    50                  55                  60

Gly Arg Phe Ser Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Leu Gly Thr Trp Ile Arg Ala Gly Pro Tyr Trp Gly Gln Gly Thr
            100                 105                 110

Gln Val Thr Val Ser Ser
        115

<210> SEQ ID NO 2
<211> LENGTH: 129
<212> TYPE: PRT
<213> ORGANISM: Vicugna pacos
<220> FEATURE:
<223> OTHER INFORMATION: VHH antibody HL22

<400> SEQUENCE: 2

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Ser Phe Thr Phe Asp
            20                  25                  30

Asp Phe Thr Ile Gly Trp Phe Arg Gln Ala Pro Gly Lys Glu Arg Glu
```

```
                  35                  40                  45
Gly Val Ser Cys Leu Ser Ser Asp Gly Ser Thr Tyr Tyr Glu Asp
            50                  55                  60

Ser Val Lys Gly Arg Phe Thr Ile Ser Ser Asp Asn Ala Lys Asn Thr
65                  70                  75                  80

Val Tyr Leu Gln Met Asn Ser Leu Lys Pro Glu Asp Thr Ala Val Tyr
                85                  90                  95

Tyr Cys Glu Ala Ala Leu Gly Arg Asn Trp Ser Pro Glu Asp Leu Cys
            100                 105                 110

Arg Ala Asp Phe Gly Ser Arg Gly Gln Gly Thr Gln Val Thr Val Ser
            115                 120                 125

Ser

<210> SEQ ID NO 3
<211> LENGTH: 127
<212> TYPE: PRT
<213> ORGANISM: Vicugna pacos
<220> FEATURE:
<223> OTHER INFORMATION: VHH antibody
<220> FEATURE:
<223> OTHER INFORMATION: Variant VHH antibody HL26

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
            35                  40                  45

Leu Cys Ile Ser Ser Ser Gly Asp Ser Thr Tyr Tyr Ala Asp Ser Val
            50                  55                  60

Lys Gly Arg Phe Thr Ile Ser Arg Asp Val Ala Lys Asn Thr Val Tyr
65                  70                  75                  80

Leu Gln Met Asn Ser Leu Lys Pro Glu Asp Thr Ala Val Tyr Tyr Cys
                85                  90                  95

Gly Thr Asp Ala Pro Tyr Tyr Ser Asp Asn Ser His Arg Cys Leu Ala
            100                 105                 110

Asp Phe Gly Ser Trp Gly Gln Gly Thr Gln Val Thr Val Ser Ser
            115                 120                 125

<210> SEQ ID NO 4
<211> LENGTH: 127
<212> TYPE: PRT
<213> ORGANISM: Vicugna pacos
<220> FEATURE:
<223> OTHER INFORMATION: VHH antibody 3bS19

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Val Ile Gly Trp Phe Arg Gln Ala Pro Gly Lys Glu Arg Glu Gly Val
            35                  40                  45

Ser Cys Ile Ser Ser Ser Asp Gly Ser Thr Tyr Tyr Ala Asp Ser Val
            50                  55                  60

Lys Gly Arg Phe Thr Ile Ser Ser Asp Asn Ala Lys Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Glu Gly Pro Thr Val Leu Asp Gly Cys Ile Val Asp Ser Gly Ser
            100                 105                 110

Tyr Tyr Phe Ser Trp Gly Gln Gly Thr Gln Val Thr Val Ser Ser
        115                 120                 125
```

<210> SEQ ID NO 5
<211> LENGTH: 118
<212> TYPE: PRT
<213> ORGANISM: Vicugna pacos
<220> FEATURE:
<223> OTHER INFORMATION: Variant VHH antibody 2bS13-97H

<400> SEQUENCE: 5

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Ser Phe Ala Ile Asn
            20                  25                  30

Asn Val Ala Trp Tyr Arg Gln Ala Pro Gly Lys Gln Arg Asp Leu Val
        35                  40                  45

Ala Leu Ile Asp Lys Tyr Asp Thr Gly Asn Ile Ala Asp Ser Val Lys
    50                  55                  60

Gly Arg Phe Ser Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

His Leu Gly Thr Trp Ile Arg Ala Gly Pro Tyr Trp Gly Gln Gly Thr
            100                 105                 110

Gln Val Thr Val Ser Ser
        115
```

<210> SEQ ID NO 6
<211> LENGTH: 118
<212> TYPE: PRT
<213> ORGANISM: Vicugna pacos
<220> FEATURE:
<223> OTHER INFORMATION: Variant VHH antibody 2bS13-100H

<400> SEQUENCE: 6

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Ser Phe Ala Ile Asn
            20                  25                  30

Asn Val Ala Trp Tyr Arg Gln Ala Pro Gly Lys Gln Arg Asp Leu Val
        35                  40                  45

Ala Leu Ile Asp Lys Tyr Asp Thr Gly Asn Ile Ala Asp Ser Val Lys
    50                  55                  60

Gly Arg Phe Ser Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Leu Gly His Trp Ile Arg Ala Gly Pro Tyr Trp Gly Gln Gly Thr
            100                 105                 110

Gln Val Thr Val Ser Ser
        115
```

```
<210> SEQ ID NO 7
<211> LENGTH: 118
<212> TYPE: PRT
<213> ORGANISM: Vicugna pacos
<220> FEATURE:
<223> OTHER INFORMATION: Variant VHH antibody 2bS13-102H

<400> SEQUENCE: 7

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Ser Phe Ala Ile Asn
            20                  25                  30

Asn Val Ala Trp Tyr Arg Gln Ala Pro Gly Lys Gln Arg Asp Leu Val
        35                  40                  45

Ala Leu Ile Asp Lys Tyr Asp Thr Gly Asn Ile Ala Asp Ser Val Lys
    50                  55                  60

Gly Arg Phe Ser Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Leu Gly Thr Trp His Arg Ala Gly Pro Tyr Trp Gly Gln Gly Thr
            100                 105                 110

Gln Val Thr Val Ser Ser
        115

<210> SEQ ID NO 8
<211> LENGTH: 118
<212> TYPE: PRT
<213> ORGANISM: Vicugna pacos
<220> FEATURE:
<223> OTHER INFORMATION: Variant VHH antibody 2bS13-100-102H

<400> SEQUENCE: 8

Gln Val Gln Leu Val Glu Ser Gly Gly Gly Leu Val Gln Ala Gly Gly
1               5                   10                  15

Ser Leu Arg Leu Ser Cys Ala Ala Ser Gly Ile Ser Phe Ala Ile Asn
            20                  25                  30

Asn Val Ala Trp Tyr Arg Gln Ala Pro Gly Lys Gln Arg Asp Leu Val
        35                  40                  45

Ala Leu Ile Asp Lys Tyr Asp Thr Gly Asn Ile Ala Asp Ser Val Lys
    50                  55                  60

Gly Arg Phe Ser Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Leu Gly His Trp His Arg Ala Gly Pro Tyr Trp Gly Gln Gly Thr
            100                 105                 110

Gln Val Thr Val Ser Ser
        115

<210> SEQ ID NO 9
<211> LENGTH: 118
<212> TYPE: PRT
<213> ORGANISM: Vicugna pacos
<220> FEATURE:
<223> OTHER INFORMATION: Variant VHH antibody 2bS13-KR5

<400> SEQUENCE: 9

Gln Val Gln Leu Val Glu Ser Gly Gly Gly Leu Val Gln Ala Gly Gly
1               5                   10                  15
```

Ser Leu Arg Leu Ser Cys Ala Ala Ser Gly Ile Ser Phe Ala Ile Asn
            20                  25                  30

Asn Val Ala Trp Tyr Arg Gln Ala Pro Gly Arg Gln Arg Asp Leu Val
        35                  40                  45

Ala Leu Ile Asp Arg Tyr Asp Thr Gly Asn Ile Ala Asp Ser Val Arg
    50                  55                  60

Gly Arg Phe Ser Ile Ser Arg Asp Asn Ala Arg Asn Thr Ala Tyr Leu
65                  70                  75                  80

Gln Met Asn Ser Leu Arg Pro Glu Asp Thr Ala Val Tyr Tyr Cys Asn
                85                  90                  95

Ala Leu Gly Thr Trp Ile Arg Ala Gly Pro Tyr Trp Gly Gln Gly Thr
            100                 105                 110

Gln Val Thr Val Ser Ser
        115

<210> SEQ ID NO 10
<211> LENGTH: 10
<212> TYPE: PRT
<213> ORGANISM: Vicugna pacos
<220> FEATURE:
<223> OTHER INFORMATION: CDR1 in VHH antibody 2bS13

<400> SEQUENCE: 10

Gly Ile Ser Phe Ala Ile Asn Asn Val Ala
1               5                   10

<210> SEQ ID NO 11
<211> LENGTH: 15
<212> TYPE: PRT
<213> ORGANISM: Vicugna pacos
<220> FEATURE:
<223> OTHER INFORMATION: CDR2 in VHH antibody 2bS13

<400> SEQUENCE: 11

Ile Asp Lys Tyr Asp Thr Gly Asn Ile Ala Asp Ser Val Lys Gly
1               5                   10                  15

<210> SEQ ID NO 12
<211> LENGTH: 12
<212> TYPE: PRT
<213> ORGANISM: Vicugna pacos
<220> FEATURE:
<223> OTHER INFORMATION: CDR3 in VHH antibody 2bS13

<400> SEQUENCE: 12

Asn Ala Leu Gly Thr Trp Ile Arg Ala Gly Pro Tyr
1               5                   10

<210> SEQ ID NO 13
<211> LENGTH: 12
<212> TYPE: PRT
<213> ORGANISM: Vicugna pacos
<220> FEATURE:
<223> OTHER INFORMATION: CDR1 in VHH antibody HL22

<400> SEQUENCE: 13

Gly Phe Ser Phe Thr Phe Asp Asp Phe Thr Ile Gly
1               5                   10

<210> SEQ ID NO 14
<211> LENGTH: 16
<212> TYPE: PRT
<213> ORGANISM: Vicugna pacos

```
<220> FEATURE:
<223> OTHER INFORMATION: CDR2 in VHH antibody HL22

<400> SEQUENCE: 14

Leu Ser Ser Ser Asp Gly Ser Thr Tyr Tyr Glu Asp Ser Val Lys Gly
1               5                   10                  15

<210> SEQ ID NO 15
<211> LENGTH: 20
<212> TYPE: PRT
<213> ORGANISM: Vicugna pacos
<220> FEATURE:
<223> OTHER INFORMATION: CDR3 in VHH antibody HL22

<400> SEQUENCE: 15

Glu Ala Ala Leu Gly Arg Asn Trp Ser Pro Glu Asp Leu Cys Arg Ala
1               5                   10                  15

Asp Phe Gly Ser
            20

<210> SEQ ID NO 16
<211> LENGTH: 10
<212> TYPE: PRT
<213> ORGANISM: Vicugna pacos
<220> FEATURE:
<223> OTHER INFORMATION: CDR1 in VHH antibody HL26

<400> SEQUENCE: 16

Gly Phe Thr Leu Asp Tyr Tyr Ala Ile Gly
1               5                   10

<210> SEQ ID NO 17
<211> LENGTH: 16
<212> TYPE: PRT
<213> ORGANISM: Vicugna pacos
<220> FEATURE:
<223> OTHER INFORMATION: CDR2 in VHH antibody HL26

<400> SEQUENCE: 17

Ile Ser Ser Ser Gly Asp Ser Thr Tyr Tyr Ala Asp Ser Val Lys Gly
1               5                   10                  15

<210> SEQ ID NO 18
<211> LENGTH: 20
<212> TYPE: PRT
<213> ORGANISM: Vicugna pacos
<220> FEATURE:
<223> OTHER INFORMATION: CDR3 in VHH antibody HL26

<400> SEQUENCE: 18

Gly Thr Asp Ala Pro Tyr Tyr Ser Asp Asn Ser His Arg Cys Leu Ala
1               5                   10                  15

Asp Phe Gly Ser
            20

<210> SEQ ID NO 19
<211> LENGTH: 10
<212> TYPE: PRT
<213> ORGANISM: Vicugna pacos
<220> FEATURE:
<223> OTHER INFORMATION: CDR1 in VHH antibody 3bS19

<400> SEQUENCE: 19

Gly Phe Thr Phe Asp Asp Tyr Val Ile Gly
1               5                   10
```

<210> SEQ ID NO 20
<211> LENGTH: 16
<212> TYPE: PRT
<213> ORGANISM: Vicugna pacos
<220> FEATURE:
<223> OTHER INFORMATION: CDR2 in VHH antibody 3bS19

<400> SEQUENCE: 20

Ile Ser Ser Ser Asp Gly Ser Thr Tyr Tyr Ala Asp Ser Val Lys Gly
1               5                   10                  15

<210> SEQ ID NO 21
<211> LENGTH: 20
<212> TYPE: PRT
<213> ORGANISM: Vicugna pacos
<220> FEATURE:
<223> OTHER INFORMATION: CDR3 in VHH antibody 3bS19

<400> SEQUENCE: 21

Ala Glu Gly Pro Thr Val Leu Asp Gly Cys Ile Val Asp Ser Gly Ser
1               5                   10                  15

Tyr Tyr Phe Ser
            20

<210> SEQ ID NO 22
<211> LENGTH: 214
<212> TYPE: PRT
<213> ORGANISM: Artificial Sequence
<220> FEATURE:
<223> OTHER INFORMATION: Chimeric antibody; Trastuzumab Fab light chain

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 23
<211> LENGTH: 449
<212> TYPE: PRT
<213> ORGANISM: Artificial Sequence
<220> FEATURE:
<223> OTHER INFORMATION: Chimeric antibody; Trastuzumab Fab heavy chain

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

-continued

```
            355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```